United States Patent [19]

Ristic et al.

[11] 4,307,191

[45] Dec. 22, 1981

[54] PROPAGATION OF BABESIA PARASITES

[75] Inventors: Miodrag Ristic, Urbana; Michael G. Levy, Champaigne, both of Ill.

[73] Assignee: University of Illinois Foundation, Urbana, Ill.

[21] Appl. No.: 130,482

[22] Filed: Mar. 31, 1980

Related U.S. Application Data

[63] Continuation-in-part of Ser. No. 34,663, Apr. 30, 1979, abandoned.

[51] Int. Cl.³ ............................................. C12Q 1/18
[52] U.S. Cl. ..................................... 435/32; 435/258; 435/947
[58] Field of Search ................. 435/32, 240, 241, 243, 435/257, 258, 947

[56] References Cited

U.S. PATENT DOCUMENTS 3,743,579 7/1973 Zilberblat ........................... 435/258

OTHER PUBLICATIONS

William Trager et al., Science, vol. 193, pp. 673–675; 1976.
Clarence A. Speer et al., Z. Parasitenk, vol. 50, pp. 237–244; 1976.
Elton E. Erp et al., Am. Four. Trop. Med. Hyg., vol. 27, No. 5, pp. 1061–1064; 1978.

*Primary Examiner*—Robert J. Warden
*Attorney, Agent, or Firm*—Merriam, Marshall & Bicknell

[57] ABSTRACT

A method for quantitative propagation of hemotropic parasites, especially Babesia parasites, in vitro, Babesia-infected erythrocyte cultures are incubated in an environment of enhanced carbon dioxide tension wherein the culture medium overlay provides a barrier to oxygen transmission such that cellular hemoglobin is essentially maintained in its deoxy state. By varying environmental carbon dioxide tension, merozoite stages of the parasite are selectively reversibly induced to migration between residence in host cells or culture medium, rendering possible the isolation of infective antigenic merozoites in large quantities. Specific Babesia antigen is harvested in large quantity from the in vitro culture medium.

16 Claims, 3 Drawing Figures

PROPAGATION OF BABESIA PARASITES

This application is a continuation-in-part of co-pending U.S. Application Ser. No. 34,663, filed Apr. 30, 1979 now abandoned.

BACKGROUND

The present invention relates generally to in vitro propagation of protozoan and rickettsial parasites and more specifically to novel methods for large scale propagation of Babesia parasites and production of extracellular Babesia antigen.

Babesia parasites are the causative agents of hemoclastic animal diseases on a world-wide basis. Tick-borne species of this genus are known to infect: cattle (*B. bovis, B. bigemina, B. divergens, B. major*); dogs (*B. canis, B. gibsoni, B. vogali*); horses (*B. equi, B. caballi*); and rodents (*B. rodhaini, B. microti*). *B. bovis* and *B. microti* are also known to be infective in humans.

Immunologically active agents have not heretofore generally been available for use as vaccine components in conferring immunity against infection by Babesia parasites. This has been due in large part to difficulties attending quantitative, in vitro propagation of Babesia parasites, and especially the difficulties inherent in separating immunologically significant materials (e.g., killed, whole antigenic merozoite stages of the parasite) from host erythrocyte cells and "contaminating" host cell components such as hemoglobin. Among the pertinent recent advances in the art of parasite propagation are disclosed in Trager, et al., *Science*, 193: pp. 673–675 (1976) and Speer, et al., *Z. Parasitenk*, 50: pp. 237–244 (1976). These references, respectively, described Plasmodium propagation in erythrocytes maintained under greatly reduced oxygen tension and continuous Plasmodium propagation in selected eukaryotic host cells. More recently, substantial advances in Babesia propagation were reported by one of the co-inventors herein and his co-workers in Erp, et al., *Am. Jour. Trop. Med. Hyg.*, 27 (5): pp. 1061–1064 (1978). Briefly put, the publication indicates that Babesia may be successfully propagated in mechanically stirred erythrocyte cultures under enhanced carbon dioxide tension and that, while the parasitic propagative methods were not suited to large scale parasite production, the results were substantially better than theretofore achieved. It is worthy of note that the attempts of Erp, et al. to propagate Babesia parasites according to the Plasmodium propagation technology of Trager, et al. were unsuccessful.

The need for even better methods of Babesia propagation has recently been amplified by the discovery of specific soluble antigenic substances producible in vitro as reported in U.S. Patent Application Ser. No. 34,664, filed Apr. 30, 1979, by Miodrag Ristic and Carlos Arellano, entitled "Babesia Antigen".

BRIEF SUMMARY

According to the present invention, methods are provided for propagation of Babesia parasites in quantities on the order of $1 \times 10^{13}$ or more times greater during 32 days of culture than heretofore obtainable by practice of the most effective prior art methods, e.g., those described in Erp, et al. Corresponding increases in production of soluble specific Babesia antigen are also obtained.

The preferred propagative procedures of the invention include static incubation of a layer of infected erythrocytes in a culture medium comprising from about 25 to 55 percent serum combined with a suitably buffered conventional erythrocyte growth promoting medium. Incubation is carried out in an atmosphere having an enhanced carbon dioxide content with the culture medium providing a static overlaying column of a depth sufficient to reduce oxygen tension and maintain erythrocytic hemoglobin essentially in a deoxy state. Specific soluble Babesia antigen is easily harvested from the growth medium.

According to another aspect of the invention, merozoite stages of Babesia parasites are obtained in quantity by discontinuation of enhanced carbon dioxide tension conditions on the incubating culture. This process results in large scale migration of merozoites into the culture medium wherein they exhibit a decreased tendency to infect host cells. Merozoites may be easily isolated from the culture medium without the difficulties ordinarily attending separation of parasites from host erythrocytes. Merozoites so obtained may be employed to secure live or killed antigen preparations, or alternately used to prepare subcultures wherein the infective tendencies of the merozoites are restored when conditions of enhanced carbon dioxide tension are reestablished.

Other aspects and advantages of the present invention will become apparent to those skilled in the art upon consideration of the following detailed description of presently preferred embodiments.

FIGS. 1 and 2 relate to vaccination test and challenge work involving soluble *Babesia bovis* antigen isolated from growth medium. FIG. 3 illustrates visually determinable aspects of in vitro propagative methods of the invention.

DETAILED DESCRIPTION

Erythrocytes suitable for use in practice of the propagative methods of the invention generally consist of a collection of cells obtained from blood of an infected animal and displaying from about 0.1 to about 5 percent infected cells. The culture medium employed consists of a combination of homologous (or as described below, heterologous) species serum obtained from a non-infected animal and a suitable erythrocyte growth promoting medium. Acceptable conventional media include Medium 199 [Grand Island Biological Corp. (GIBCO)] and RPMI 1640 (GIBCO). Beneficial effects are noted when the glucose content of such media is augmented. By way of example, excellent results are obtained by use of Medium 199 wherein glucose concentration is adjusted upward from 5.55 mM to about 16.5 mM.

The serum component of the culture medium may be provided in quantities ranging from an effective minimum of about 25 up to about 55 percent by volume, and preferably about 40 percent. A culture medium containing less than about 25 percent serum will not optimally provide parasite propagation, while use of 55 percent or more serum provides no substantially increased rate of propagation. The culture medium will ordinarily include one or more antibiotics such as penicillin or streptomycin, and will be buffered with conventional buffering substances such as HEPES, TRIS, and the like.

Infected erythrocytes are added to culture medium to reach a final concentration of 4 to 11 and preferably about 9 percent and the pH is adjusted (with acid or base, depending on the buffer employed) to about 6.9 to 7.4 and preferably about 7.0. Some degree of modification of medium pH may be appropriately geared to the particular species of parasite propagated. *Babesia bovis*, for example, is best continuously propagated at a pH of about 7.0 and *B. canis* at about pH 7.3. Cultures are incubated at a temperature of from 35° to 38° C. and preferably 37° C. in an atmosphere of air augmented to include about 3 to 7 percent, and preferably 5 percent, carbon dioxide. Temperatures of up to about 41°–42° C. will not have serious deleterious effects unless maintained for long periods of time. The depth of the culture medium overlaying the settled cells is adjusted to from about 0.5 to about 0.8 cm and preferably about 0.62 cm under the atmospheric conditions described above, thus providing an operative barrier to rapid oxygen transmission from the atmosphere to the parasite and host cells.

Figure 3:
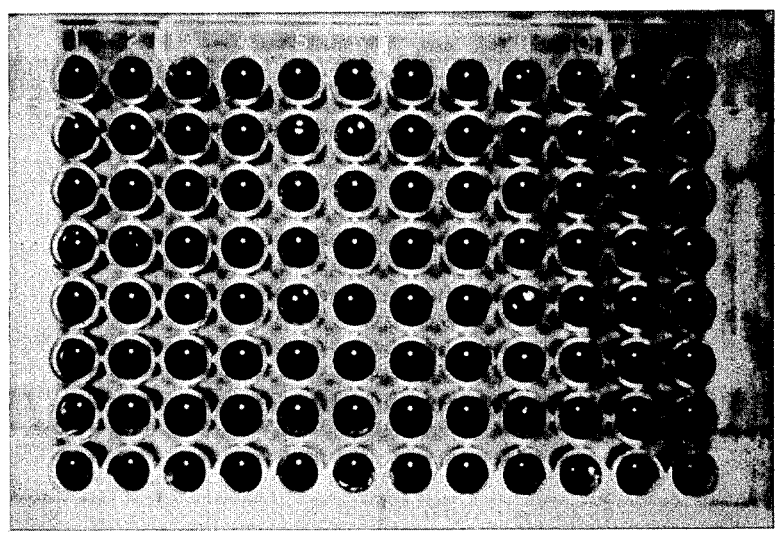

Substantial variations in culture medium depth are acceptable provided that appropriate adjustments are made in the relative oxygen and carbon dioxide content of the atmosphere. As a rule, these factors should be operatively adjusted to obtain such conditions as will result in the erythrocytic hemoglobin being maintained in its deoxy state—as indicated by the cells having a dark red to "black" color. As one example, such conditions are obtained with the air/5 percent carbon dioxide atmosphere when the medium is about 0.62 cm deep, but not when the medium is only 0.16 cm deep. It is further noteworthy that the same medium depth and atmospheric conditions as result in maintenance of hemoglobin of Babesia infected cells in the deoxy state do not provide the same result in a non-infected culture of erythrocytes. FIG. 3 consists of a photographic representation of a 96-well microtiter plate wherein alternating pairs of rows comprise Babesia-infected and non-infected erythrocyte cultures incubated under identical conditions. Within a period beginning a few hours after commencement of incubation, hemoglobin in infected cells begins to exhibit a darkened color characteristic of the deoxy state (rows 3–4, 7–8, and 11–12 from the left) while non-infected cells show a normal light red color. Present information indicates, therefore, that the described phenomenon is peculiar to parasite infected cells and essential to rapid propagation of parasites.

Propagative methods of the invention are most suitably carried out under static conditions, i.e., in the absence of regular and substantial agitation of the culture. Such agitation, as a practical matter, makes the required maintenance of erythrocytic hemoglobin in a deoxy state inordinately difficult. The deoxy state for host cell hemoglobin was not maintained, for example, in an agitated experimental culture, even though the culture atmosphere had been modified to contain only about 2 percent oxygen. Substantial agitation of cultures of the invention also appears to promote physical aggregation of extracellular merozoites, thus generally diminishing their capacity to infect erythrocytic hosts. In sum, although not unequivocally established to be essential, incubating cultures of the invention statically is the much preferred practice.

Continuity of the cultures is easily maintained by changing the medium on a daily basis. Subcultures are prepared at 48 to 72 hour intervals by diluting infected cultures with fresh cultures containing uninfected erythrocytes in ratios of from about 1:3 to about 1:20. During medium change and subculturing, the darkened color of the cells in culture temporarily diminishes.

Isolation of soluble specific Babesia antigen from culture medium is accomplished by conventional centrifugation and selective precipitation techniques. Isolation of merozoites from the culture medium is accomplished by selective centrifugation of the culture to effect separation from host cells.

When it is desired to obtain large quantities of merozoite stages of Babesia parasites from the cells of the culture, conventional separatory techniques (use of pressure cells and the like) may be employed. A vastly more convenient method is provided according to that aspect of the invention which directs discontinuation of atmospheric conditions of increased carbon dioxide tension (i.e., a change in atmosphere to pure air). If practiced from 4 to 16 hours prior to expected merozoite harvesting, this procedure will have the result of inducing the migration of substantial numbers of merozoites from host cells into the medium.

Accompanying this surprising migratory phenomenon is an apparent reversible reduction in the tendency of the merozoites to infect host cells. Put another way, the normal phenomenon of merozoite migration from a host cell, followed almost immediately by infection of another cell, is not observed. Rather, the merozoites remain in the culture medium after leaving host cells. Perhaps more remarkable is the observation that infectivity of merozoites may be restored by an alteration of atmospheric conditions to restore an increased carbon dioxide tension. This occurs not only in the "original" culture but also after transfer to subcultures, further indicating that merozoite infectivity (as well as propagation) is highly sensitive to changes in carbon dioxide tension on the medium.

The following examples illustrate practice of the invention and more specifically relate to: methods for propagation of *Babesia bovis* in a bovine erythrocyte culture; and, a comparison of effectiveness of methods of the invention to the methods of Erp, et al; tests of effectiveness, as a vaccine component, of antigen obtained by the invention; determination of optimal erythrocyte and serum sources; and propagation of non-Babesial hemotropic parasites.

EXAMPLE 1

A culture medium is prepared consisting of 40% fresh, defibrinated bovine serum and 60% Medium 199 supplemented with 25 mM HEPES buffer and containing both 100 units of penicillin and 100 μg. streptomycin per ml. Bovine erythrocytes displaying from 0.1 to 5% (of total population) infection with *Babesia bovis* are added to the medium to a concentration of 5 to 8%. The pH is then adjusted to 7.0 using 1 N HCl, the cultures are plated out in a manner providing for a column of medium 0.62 cm. deep overlaying the settled cells, and then incubated at 37° C. in an atmosphere consisting of air augmented to include 5% carbon dioxide and saturated with water vapor. Medium is changed daily and subcultures are prepared at 48 to 72 intervals by dilution (1:3 to 1:20) with an identical culture medium containing 5–8% uninfected bovine erythrocytes. Cultures are routinely monitored microscopically for parasitemia. Calculations regularly indicate that after 3 days of incubation, approximately 80 percent of the erythrocyte host cells harbor parasites. Parasite multiplication over a period of 44 days is on the order of $1.69 \times 10^{26}$ fold.

EXAMPLE 2

*Babesia bovis* parasites were propagated according to the methods described in Erp, et al. for a period of 32 days. Parasites were multiplied by a factor of $6.4 \times 10^5$ with a cumulative dilution of $1.92 \times 10^5$. The method of Example 1 was carried out for comparative purposes. After 32 days a cumulative increase in parasites of $1.72 \times 10^{10}$-fold was obtained with a cumulative dilution of $4.84 \times 10^9$. Repetitions of the Example 1 for comparative purposes provided cumulative increases in parasites up to about $3.7 \times 10^{17}$ over 32 days.

Consistent with the above, practice of the invention is expected to provide for large scale production (and accumulation in the culture medium) of specific, cell-free soluble Babesia antigens. Merozoite stages of Babesia parasites obtained according to the invention are useful whole (live or killed) as antigenic materials for use in vaccines or as a source of soluble antigen which is also useful as a vaccine component.

EXAMPLE 3

Figure 1:
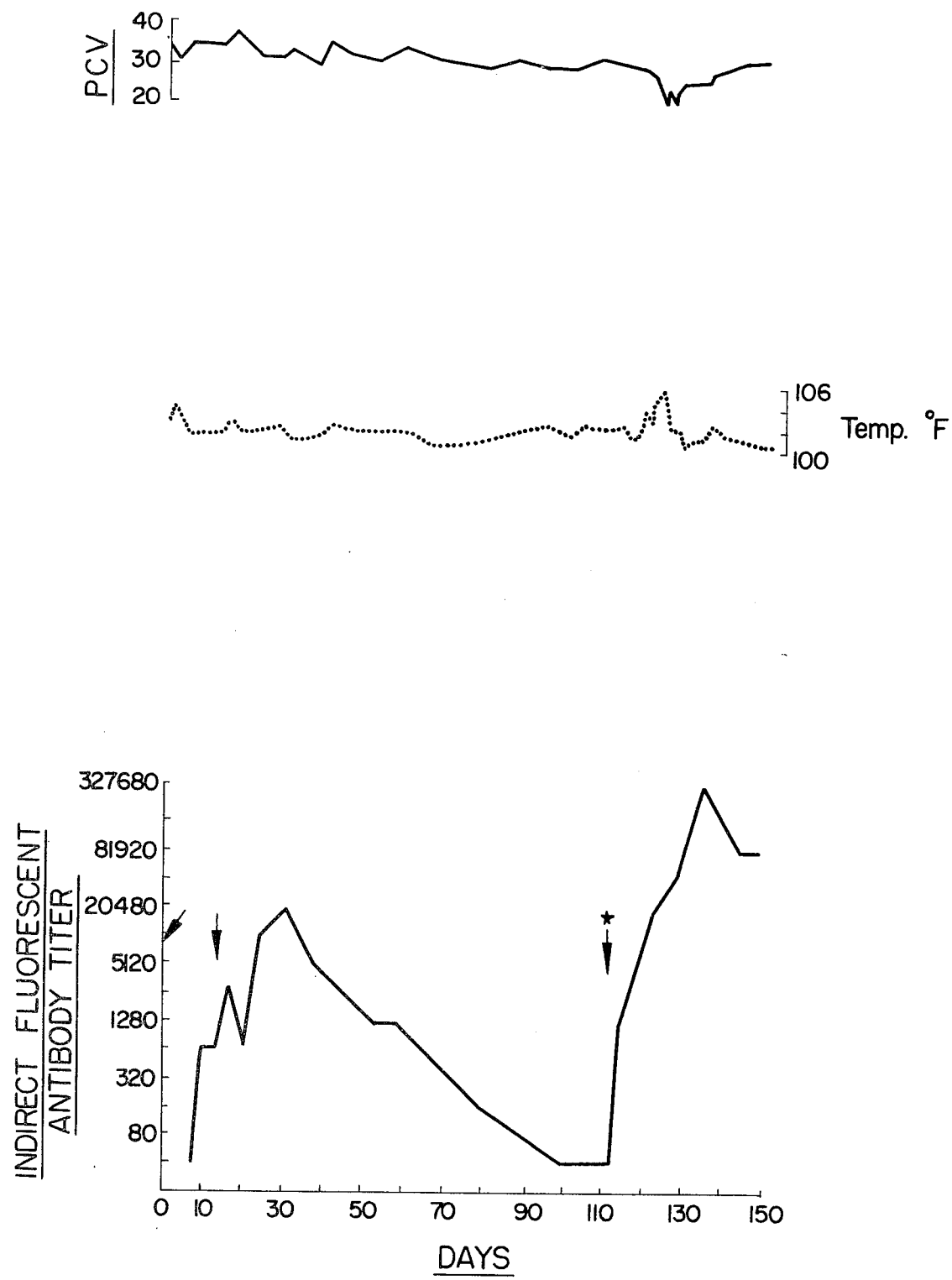
Figure 2:
Figure 2:
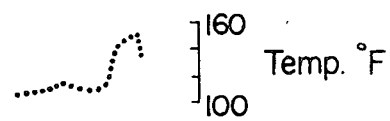
Figure 2:
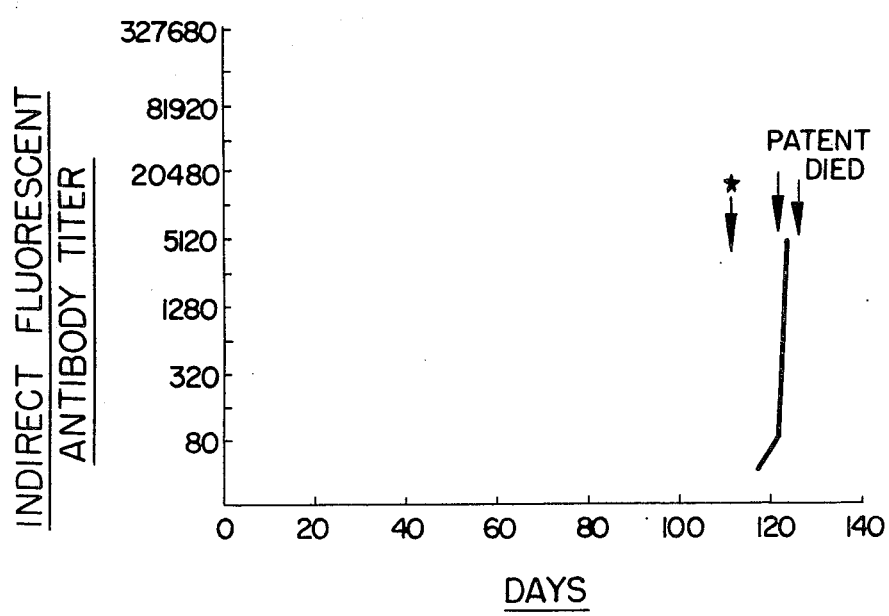

FIGS. 1 and 2 illustrate in part the results of a test of the in vivo biological activity characteristic of the soluble antigen obtainable from the culture medium upon practice of the propagation methods of the invention. A vaccine was prepared from culture supernatant obtained by practice of the general procedures of Example 1. Each dose contained the lyophilized soluble antigen fraction isolated from 10 ml of culture supernatant (wherein the average parasitemia following 3 days of in vitro propagation was about 16.4 percent) reconstituted with 1 ml water and 1 mg of saponin adjuvant (Quil-A, Superflos A/G, Vedback, Denmark, available from Accurate Chemical & Scientific Co., Hicksville, New York). Two adult Holstein cows were used in the study and monitored for varitions in Babesia serum antibodies (expressed as IFA titer), variations in rectal temperatures (expressed in °F.) and variations in packed cell volume of blood (expressed as a percentage of total blood volume). FIG. 1 provides data for the experimental animal and FIG. 2 provides data for the control animal. The experimental cow was injected with a first dose of the vaccine on day 0 and a second dose on day 14 (noted by the unstarred arrows in FIG. 1). Antibody titers for the experimental animal rose to a peak at about day 35 and then gradually diminished. Temperature and packed cell volume data remained relatively constant. At day 112, both the experimental and control animals were challenged by intramuscular injection of $1 \times 10^8$ virulent Babesia bovis ) noted by the starred arrows in FIGS. 1 and 2). Antibody titers rose precipitously in the experimental animal almost immediately, indicating a true anamnestic immune response. While body temperature rose, it returned to normal in a few days. Similarly, packed cell volume diminished somewhat but soon returned to normal ranges. The control animal, on the other hand, showed no antibody development until nearly ten days following challenge at which time parasites were patent in blood smears, temperature had risen steadily and packed cell volume had dropped precipitously. On day 124 the control animal died. The vaccinated experimental animal was a long term survivor.

EXAMPLE 4

The sterile immunity characteristics derived by the practice of vaccination with antigen obtained according to the invention are illustrated by the absence of infectivity of blood of vaccinated animals. More particularly, for examle, 50 ml of blood of the experimental animal of Example 3 was withdrawn 28 days after challenge (i.e., about day 140) and injected into the circulatory system of a splenectomized calf. The calf failed to become infected even though it was later shown to be susceptible to infection by challenge with Babesia bovis.

EXAMPLE 5

Propagative methods of the invention generally provide the most substantial advantages when both erythrocytes and serum are obtained from animals at growth stages wherein factors contributing to natural immunity to parasite infection are absent or suppressed. As one example, calves up to about 3 months of age generally exhibit a gradually diminishing degree of immunity of infection by Babesia bovis. Rather expectedly, in vitro cultures of the invention wherein such calf erythrocyte cells and/or serum are employed to propagate Babesia bovis are markedly less successful than cultures involving adult bovine blood components. Table 1 below provides the results of experimentation with Babesia bovis propagation in cultures including fresh adult and calf bovine blood components. Calf erythrocytes and serum were obtained from animals less than 10 days old. The results reflect the mean cumulative parasite increase factors for a total of 7 experiments, each involving 3 subcultures of two days duration with serum and erythrocyte source as indicated.

TABLE 1

| Erythrocyte Source | Serum Source | Cumulative Increase |
|---|---|---|
| Adult | Adult | 5893 |
| Calf | Adult | 1408 |
| Adult | Calf | 423 |
| Calf | Calf | 18 |

As a general rule, commercially prepared defibrinated serum obtained from fetal calves, newborn calves and bobby calves is not a suitable component for in vitro propagation of Babesia bovis according to the invention, even if adult bovine erythrocytes are employed.

While the above Examples treat Babesia bovis propagation in bovine erythrocytes, the procedures described therein are equally applicable to propagation of other Babesia species in appropriate host animal erythrocytes. The methods of the invention are expected to be additionally applicable to propagation of selected Babesia species in erythrocytes of animal species other than those normally infected by the selected species—thus providing for merozoites having attenuated infectivity and consequent exceptional utility as live vaccine components.

EXAMPLE 6

A series of experiments was carried out to determine the general effects of use of heterologous species erythrocytes and serum on propagation of Babesia bovis according to the invention.

In a first experiment, Babesia bovis was propagated according to Example 1 in a culture of bovine erythrocytes and buffered 40% bovine serum medium. Three subcultures were developed using fresh bovine erythrocytes. Of these three, the "control" subculture was continued in bovine serum; the first test subculture was continued using horse serum; and the second test culture was continued using a mixture of three parts horse serum and 5 parts bovine serum. Notations of percent parasitemia were made after 1, 2 and 3 days of propagation of the subcultures and the data obtained is set out in Table 2 below.

TABLE 2

| Medium | 1 Day | 2 Days | 3 Days |
|---|---|---|---|
| Bovine Serum | 2.9 | 4.2 | 8.5 |
| Horse Serum | 1.4 | 5.5 | 1.6 |
| Horse/Bovine Serum | 5 | 11.4* | 15.3* |

*Evidence of hemolysis noted. Free parasites.

A second experiment was conducted according to the procedure set out immediately above but wherein rabbit serum was employed in place of horse serum. The results are set out in Table 3.

TABLE 3

| | Percent Parasitemia | | |
|---|---|---|---|
| Medium | 1 Day | 2 Days | 3 Days |
| Bovine Serum | 3 | 4.9 | 6.6 |
| Rabbit Serum | 2.2 | 3.5 | 4.8 |
| Rabbit/Bovine Serum | 3.5 | 24.8 | 70.3* |

*Evidence of hemolysis noted. Free parasites.

Another series of experiments was conducted wherein both host erythrocytes and serum component were subject to variation. Infection of erythrocytes was noted in all of the following *Babesia bovis* culture combinations of erythrocyte/serum sources: ovine/bovine; ovine/ovine; goat/bovine; goat/goat; horse/bovine; horse/horse; rabbit/bovine; and rabbit/rabbit. Only the last three noted cultures exhibited substantially continuous muliplication of parasites and some degree of hemolysis was noted in each of the heterologous combinations. Similar experiments showed that levels of from 10–15 and 8–11 percent parasitemia were obtained in homologous rabbit/rabbit and horse/horse culture systems.

The procedures of the invention are also expected to be useful in propagation of hemotropic protozoan parasites of differing genera, especially those of the genus Plasmodium, as well as with rickettsial parasites such as *Anaplasma marginale*.

EXAMPLE 7

An experiment was conducted to ascertain the effectiveness of propagation of non-Babesia parasites by the procedures of the invention. Example 1 was repeated using bovine host erythrocytes infected with *Anaplasma marginale* and 30 percent defibrinated calf serum from an infected calf. Parsitemia was elevated over the first three days from a 1.1 percent initial level to 7.4 percent. Following subculture during which parasitemia was reduced to 1.5 percent by addition of fresh erythrocytes, there was an increase to 3.6 percent in one day, after which parasitemia remained stable. The experiment was terminated on the sixth day after initiation upon notation of abnormal parasitic morphology. The cumulative increase in parasites over the first four days of the procedure was about 15-fold.

Numerous modifications and variation in the practice of the invention are expected to occur to those skilled in the art upon consideration of the foregoing description. As one example the propagative methods of the present invention are useful in the process of screening proposed anti-Babesia therapeutic agents for effectiveness without any need for testing on infected animals. According to this procedure, varying dosage amounts of the agents are administered directly to the culture medium prior to incubation and the cultures are monitored for the presence or absence of darkened, deoxy-state, hemoglobin. In one such screening procedure, cultures containing differing amounts of DL-(4-amidinophenyl)-triazan-(N-1,3)-diaceturate were added to cultures having an initial parasitemia of 0.2 to 0.5%. After incubation under conditions as described in Example 1 for 24 to 48 hours, it was found that accepted therapeutic levels of the agent ($3.5 \times 10^{-6}$ g/ml) prevented parasite growth, as was evidenced by the presence of normal light red erythrocyte color in the infected cells. Controls and cultures having lower levels of the anti-*Babesia bovis* drug (e.g., $3.5 \times 10^{-8}$ g/ml) exhibited the darkened color characteristic of hemoglobin in the deoxy state.

As another example, collections of merozoite stages of Babesia obtained by the methods of the invention may be employed to test for the presence, in a fluid sample, of specific antibodies to Babesia. Such antibodies would inhibit the infectivity of merozoites when incorporated in cultures according to the invention which are ordinarily supportive of rapid infection of host cells. Inhibition of infectivity could be monitored on the basis of parasitemia determinations or even the presence or absence of the darkened color characteristic of host erythrocyte hemoglobin in the deoxy state. Further, determinations of specific Babesia antigen can be carried out by observation of the extent to which inhibition of merozoite infectivity by antibodies is diminished by incubation with an antigen-containing sample.

What is claimed is:

1. In the method for in vitro propagation of Babesia parasites by incubation in a culture medium containing erythrocyte host cells, the improvement comprising:
   (1) providing as a component in said culture medium from about 25 to about 55 percent defibrinated serum; and
   (2) carrying out said incubation step,
      (a) in the presence of a controlled atmosphere containing 3 to 7 percent carbon dioxide, and
      (b) under conditions of reduced oxygen tension upon the infected erythrocytes resulting in maintenance of erythrocytic hemoglobin in its deoxy state.

2. The method of claim 1 wherein said incubation step is carried out statically.

3. The method of claim 2 wherein said incubation step is carried out at from 35° to 38° C., in an atmosphere comprising air augmented to contain about 5 percent carbon dioxide and wherein conditions of reduced oxygen tension are secured by maintaining the depth of medium above the host cells at from about 0.5 to 0.8 cm.

4. The method of claim 1 further including the post-incubation step of harvesting Babesia parasites from the culture medium.

5. The method of claim 4 further including reducing the carbon dioxide content of said controlled atmosphere for from about 4 to about 16 hours prior to harvesting parasites from the culture medium.

6. The method of claim 1 further including the post-incubation step of harvesting specific soluble Babesia antigens from the culture medium.

7. The method of claim 1 wherein said erythrocyte host cells and said defibrinated serum are derived from the same species of animal.

8. The method of claim 1 wherein the Babesia parasite propagated are of the species, *Babesia bovis*.

9. In a method for in vitro propagation of *Babesia bovis* parasite by incubation in a culture medium containing bovine erythrocyte host cells, the improvement comprising:

(1) providing as a component in said culture medium from about 25 to about 55 percent defibrinated bovine serum; and (2) carrying out said incubation step, (a) in the presence of a controlled atmosphere containing 3 to 7 percent carbon dioxide, and (b) under conditions of reduced oxygen tension upon infected erythrocytes resulting in maintenance of erythrocytic hemoglobin in its deoxy state.

10. The method of claim 9 further including the post-incubation step of harvesting *Babesia bovis* antigen from the culture medium.

11. In the method for in vitro propagation of hemotropic parasites by incubation in a culture medium containing erythrocyte host cells, the improvement comprising:

(1) providing as a component in said culture medium from about 25 to about 55 percent defibrinated serum; and (2) carrying out said incubation step, (a) statically, (b) in the presence of a controlled atmosphere containing 3 to 6 percent carbon dioxide, and (c) under conditions of reduced oxygen tension upon the infected erythrocytes resulting in maintenance of erythrocytic hemoglobin in its deoxy state.

12. The method of claim 11 further including the post-incubation step of harvesting hemotropic parasites from the culture medium.

13. The method of claim 12 further including reducing the carbon dioxide content of said controlled atmosphere for from about 4 to about 16 hours prior to harvesting parasites from the culture medium.

14. The method of claim 11 wherein said hemotropic parasite is of the genus Plasmodium.

15. The method of claim 11 wherein said hemotropic parasite is of the genus Anaplasma.

16. A method for determining the anti-Babesia effectiveness of a substance, said method comprising adding the substance to an erythrocyte culture of Babesia parasites propagated according to claim 1 and monitoring said culture for the presence or absence of erythrocytic hemoglobin in its deoxy state, wherein the absence of erythrocytic hemoglobin in its deoxy state is a presumptive indication of the anti-Babesia effectiveness of the substance.

* * * * *